(12) United States Patent
Kiraly et al.

(10) Patent No.: US 9,260,421 B2
(45) Date of Patent: Feb. 16, 2016

(54) PHARMACEUTICAL INTERMEDIATES AND PROCESS FOR THE PREPARATION THEREOF

(75) Inventors: Imre Kiraly, Budapest (HU); Tibor Szabo, Budapest (HU); Gyula Simig, Budapest (HU); Balazs Volk, Budapest (HU); Laszlo Szlavik, Budapest (HU); Jozsef Barkoczy, Budapest (HU); Gyorgy Ruzsics, Budapest (HU); Gyula Lukacs, Budapest (HU); Laszlo Pongo, Kerepes (HU); Andras Boza, Budapest (HU); Maria Tothne Lauritz, Budapest (HU); Maria Kovacs, Budapest (HU)

(73) Assignee: EGIS GYOGYSZERGYAR NYILVANOSAN MUKODO RESZVENYTARSASAG, Budapest (HU)

( * ) Notice: Subject to any disclaimer, the term of this patent is extended or adjusted under 35 U.S.C. 154(b) by 50 days.

(21) Appl. No.: 14/116,464

(22) PCT Filed: May 10, 2012

(86) PCT No.: PCT/HU2012/000036
§ 371 (c)(1),
(2), (4) Date: Feb. 12, 2014

(87) PCT Pub. No.: WO2012/153158
PCT Pub. Date: Nov. 15, 2012

(65) Prior Publication Data
US 2014/0155614 A1    Jun. 5, 2014

(30) Foreign Application Priority Data

May 11, 2011    (HU) .................... 11 00244

(51) Int. Cl.
*C07D 271/06*    (2006.01)
*C07D 413/14*    (2006.01)
*C07D 401/12*    (2006.01)

(52) U.S. Cl.
CPC ............ *C07D 413/14* (2013.01); *C07D 271/06* (2013.01); *C07D 401/12* (2013.01)

(58) Field of Classification Search
CPC ... C07D 271/06; C07D 413/14; C07D 401/12
USPC .............. 546/269.1, 273.4; 548/131; 514/364
See application file for complete search history.

(56) References Cited

U.S. PATENT DOCUMENTS

| 6,245,914 B1 * | 6/2001 | Ma et al. ............. 548/131 |
| 6,248,770 B1 | 6/2001 | Ries et al. |
| 7,202,368 B2 | 4/2007 | Zerban et al. |
| 7,459,566 B2 | 12/2008 | Zerban et al. |
| 8,354,543 B2 | 1/2013 | Zerban et al. |
| 8,471,033 B2 | 6/2013 | Filser et al. |
| 2001/0006977 A1 | 7/2001 | Ries et al. |
| 2003/0004356 A1 | 1/2003 | Ries et al. |
| 2006/0004064 A1 | 1/2006 | Zerban et al. |
| 2007/0149589 A1 | 6/2007 | Zerban et al. |
| 2007/0185333 A1 | 8/2007 | Zerban et al. |
| 2010/0210845 A1 | 8/2010 | Zerban et al. |
| 2011/0118471 A1 | 5/2011 | Filser et al. |

FOREIGN PATENT DOCUMENTS

| WO | 2006000353 A1 | 1/2006 |
| WO | 2007071742 A1 | 6/2007 |
| WO | WO 2009/111997 | * 9/2009 |
| WO | 2009153215 A1 | 12/2009 |
| WO | 2012077136 A2 | 7/2012 |

OTHER PUBLICATIONS

Eloy; Fortschr. Chem. Forsch., 1965, Bd. 4, S. 807-876.*
Hemming; "1,2,4-Oxadiazoles." In Comprehensive Heterocyclic Chemistry III., 2008, Elsevier, London, UK, pp. 243-314.*
Sendzik; Tetrahedron Letters, 2003, 44, 8697-8700.*
International Search Report for PCT/HU2012/000036 dated Aug. 30, 2012.
"Intermediates of N-(2-(4-(N-(Hexyloxycarbonyl) amidino) phenylamino methyl)-1-methyl-H-benzinnidazol-5-ylcarbonyl)-N-(2-pyridyl)-beta-alanine ethyl ester," IP.COM Journal, Feb. 23, 2009, XP013129680.

* cited by examiner

*Primary Examiner* — Janet L Andres
*Assistant Examiner* — Daniel Carcanague
(74) *Attorney, Agent, or Firm* — Millen White Zelano and Branigan, PC; Csaba Henter; Anthony Zelano

(57) ABSTRACT

The present invention relates to a process for the preparation of dabigatran etexilate of the formula

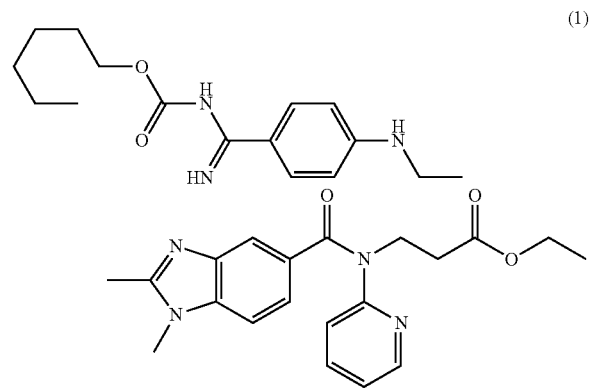

(1)

or pharmaceutically accepted salts thereof.

26 Claims, No Drawings

PHARMACEUTICAL INTERMEDIATES AND PROCESS FOR THE PREPARATION THEREOF

TECHNICAL FIELD OF THE INVENTION

This invention relates to a new and advantageous manufacturing process of dabigatran etexilate and new intermediates of said synthesis route.

KNOWN TECHNICAL BACKGROUND OF THE INVENTION

It is known that ethyl-3-[(2-{[4-(hexyloxycarbonylamino-imino-methyl)-phenylamino]-methyl}-1-methyl-1H-benzimidazole-5-carbonyl)-pyridin-2-yl-amino]-propionate having the INN dabigatran etexilate of the Formula (1)

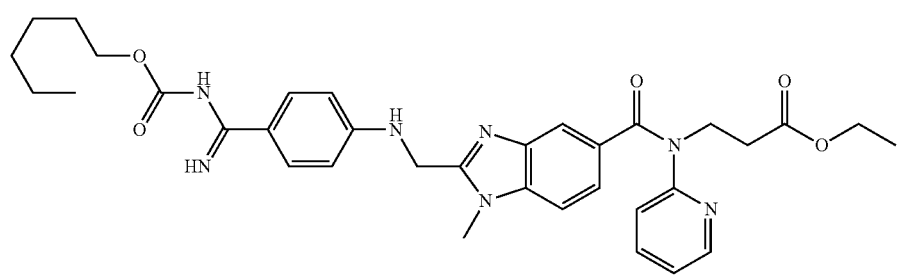

is an oral anti-coagulant of a thrombine inhibitory mechanism.

Dabigatran etexilate was first described by Hauel et al in EP 966 454 (Hungarian equivalent HU 223 754). The dabigatran etexilate base of the Formula 1 is prepared by the synthesis route shown on reaction scheme 1. In the last step the hydrochloride salt of the amidine of the Formula (2)

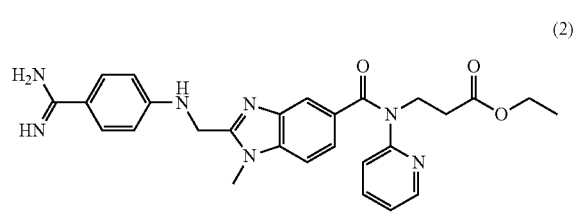 [SMILES: CCOC(=O)CCN(C(=O)c1ccc2c(c1)nc(CNc1ccc(C(=N)N)cc1)n2C)c1ccccn1]

is coupled with the hexyl chloro formiate of the Formula (3)

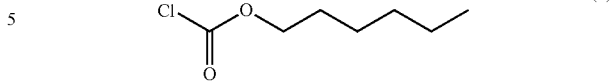

The key step of the synthesis route is the conversion of the nitrile of the Formula (4)

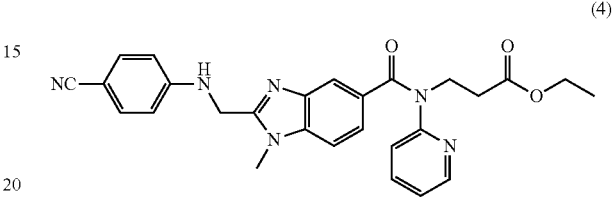

into the amidine/$2^X$HCl//Pinner reaction/. The low yields of the Pinner reaction can be derived from the water sensibility of the reaction on the one hand while the realization of the reaction is rendered more difficult on the other by the fact that the ester function of the molecule is susceptible to hydrolysis. According to Example 58b of said patent—in an analogous manner to Example 25d 1.2 g of 1-methyl-2-[N-(cyanophenyl)-aminomethyl]-5-benzimidazole-carboxylic acid-N-(2-pyridyl)-N-[2-(ethoxycarbonylethyl]-amide (4) is reacted with ethanol saturated with hydrochloric acid in large dilution. The evaporated crude product is then converted with 100 ml of ethanol and ammonium carbonate into the hydrochloric acid salt of 1-methyl-2-[N-(4-amidinophenyl)-aminomethyl]-5-benzimidazole-carboxylic acid-N-(2-pyridyl)-N-[2-(ethoxycarbonyl)-ethyl]-amide (2). Said compound is purified by repeated removal of the solvent and column chromatography. The base thus obtained (1) is characterized only by TLC $R_f$ value and mass chromatography data. Thus it does not appear whether the product is crystalline or amorphous.

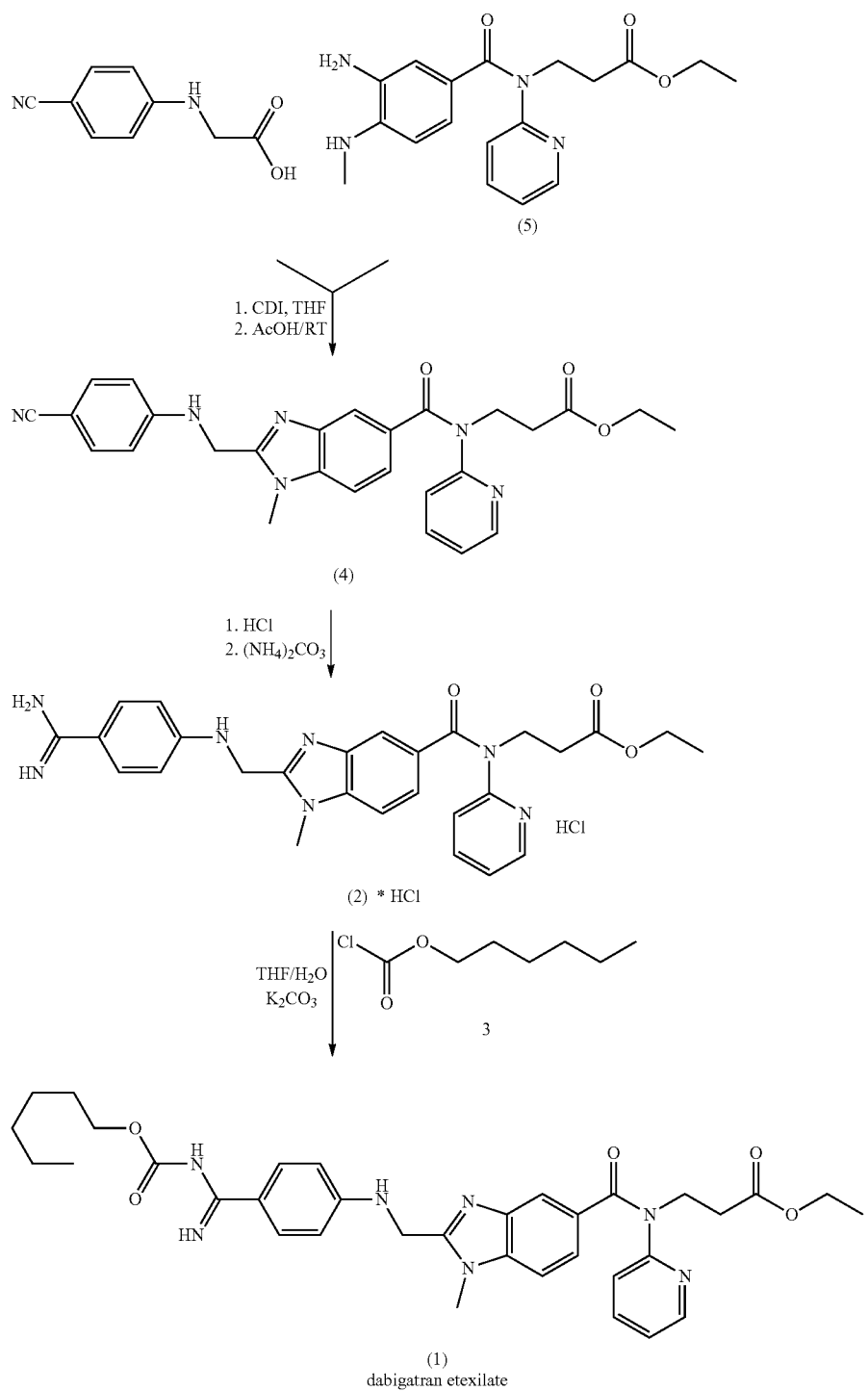

(1) dabigatran etexilate

The synthesis route of dabigatran etexilate according to the basic patent is shown on reaction scheme 1.

The purification step performed by using large dilutions and column chromatography makes the scaling up and industrial scale realization of the process impossible or strongly limited. According to Example 113 the last step (2·$^x$HCl to 1) is carried out by coupling 1-methyl-2-[N-(4-amidino-phenyl)-aminomethyl]-5-benzimidazole-carboxylic-acid-N-(2-pyridyl)-N-[2-(ethoxycarbonyl-ethyl]-amide (2·$^x$HCl) and hexyl chloro formiate (3). The total yield of the process/5→1/ is only 22%, related to the 3-amino-4-(methylamino-benzoic) acid-N-[2-/ethoxycarbonyl-ethyl]-amide (5) starting material.

In their article (J. Med. Chem. 2002, 45, 1757-1766) Hauel et al describe a process identical with that set forth in the basic patent but the preparation of the coupling agent (5) is explained in details on reaction scheme 2. via the amino-nitro compound of the Formula

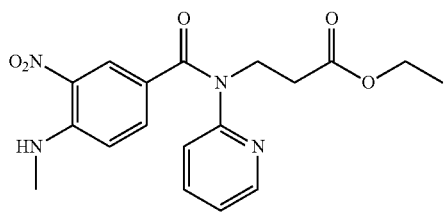
(6)
The dabigatran etexilate base/1/is characterized by mass spectrum, 1H NMR and melting point (128-129° C.). The latter value is identical with that indicated later for the anhydrous III modification (WO 2008/059029 Tmp=128±3° C.).
The broadened synthesis route of dabigatran etexilate is shown on reaction sequence 2 (J. Med. Chem. 2002, 45, 1757-1766).
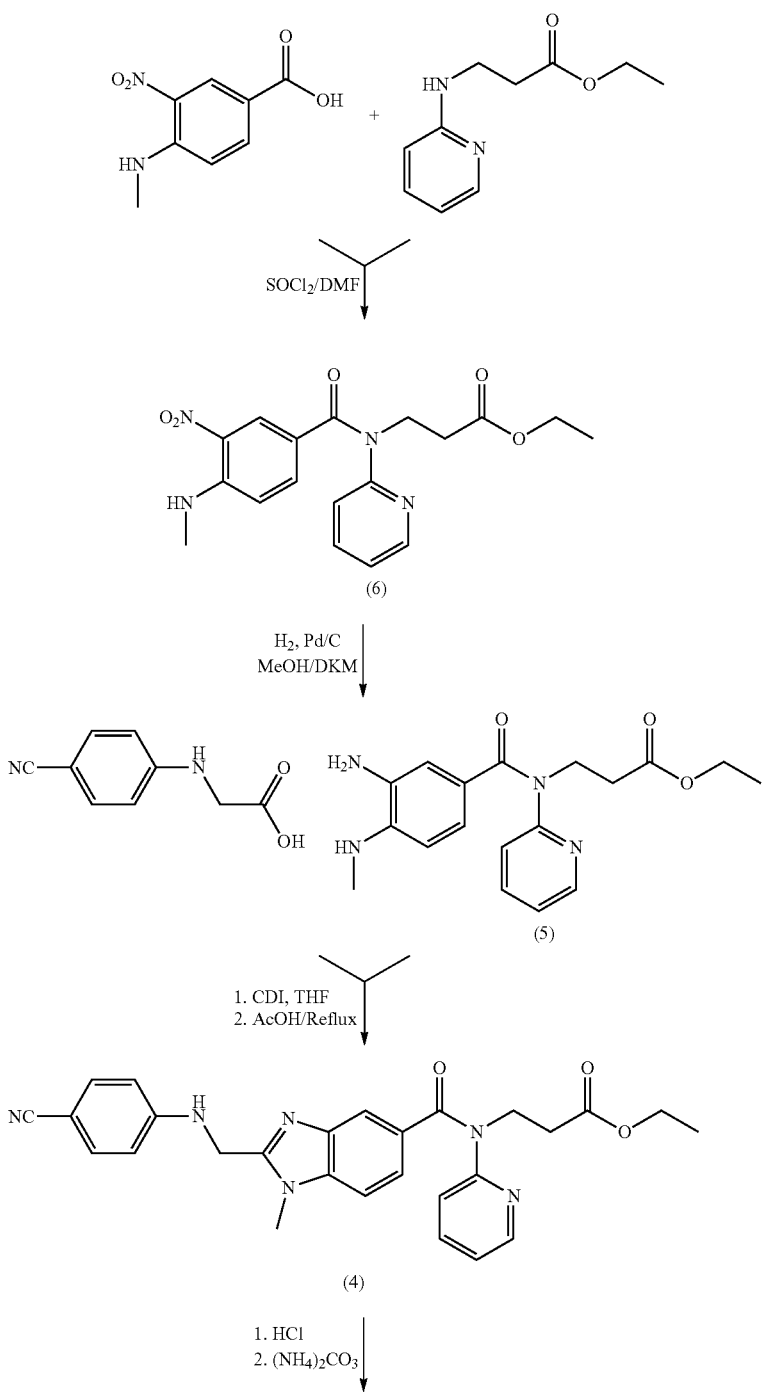

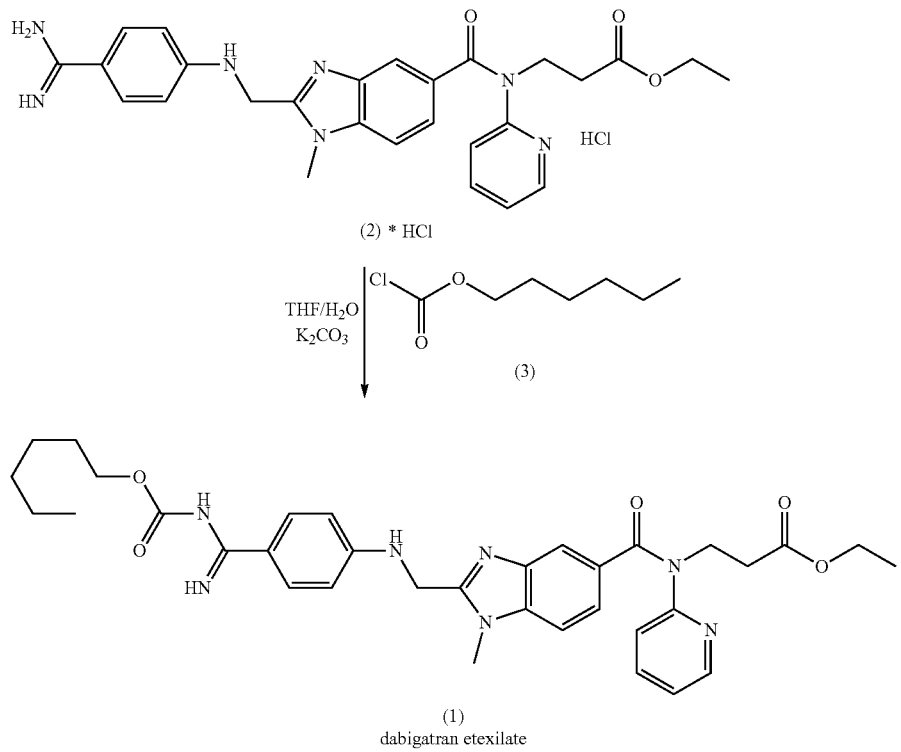

(2) * HCl

THF/H₂O
K₂CO₃

(3)

(1)
dabigatran etexilate

A new synthesis route of dabigatran etexilate is disclosed in WO 2006/000353. The steps of the synthesis are shown on reaction sequence 3. This synthesis route contains more steps than the process described in the basic patent. According to Examples 1 and 2 the 2-[4-(1,2,4-oxadiazole-5-on-yl)-phenylamino]acetic acid of the Formula

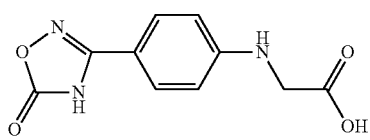

is prepared in several steps; said compound contains the necessary amidino group in a cyclic form. This compound is coupled with 3-amino-4-(methylamino)-benzoic acid-N-[2-(ethoxycarbonyl-ethyl]-amide (5) according to the method described in the basic patent. In Example 3 the coupling step is described in three variants (A. B C) to yield the diacetate salt of 1-methyl-2-{N-[4-(1,2,4-oxadiazole-5-one-3-yl)-phenyl]-amino/methyl}-benzimidazole-5-yl-carboxylic acid-N-(2-pyridyl/-N-[2-(ethoxycarbonyl-ethyl]-amide of the Formula

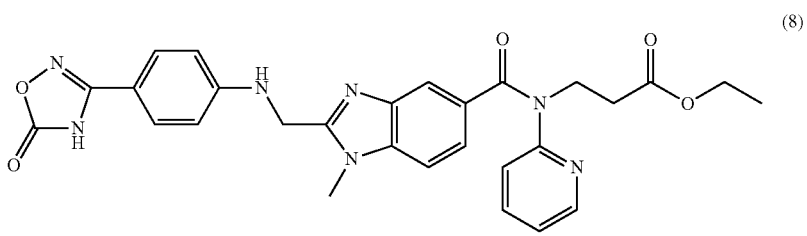 [SMILES: CCOC(=O)CCN(C(=O)c1ccc2c(c1)nc(CNc1ccc(-c3noc(=O)[nH]3)cc1)n2C)c1ccccn1]

In the coupling reaction 1,1'carbonyl-diimidazole (CDI), triproplyl-phosphonic acid anhydride (T3P) or pivaloyl chloride is used as auxiliary reactant. From the diacetate salt of (8) by hydrogenation and addition to the crude product an excess of p-toluenesulfonic acid the tosylate salt of 1-methyl-2-[N-(4-amidino-phenyl)-aminomethyl]-5-benzimidazole-carboxylic acid-N-(2-pyridyl)-N-[2-(ethoxy-carbonyl)-ethyl]-amide (2) is obtained. In Examples 4A, 4B and 4C a base:acid ratio of 1:1 is stipulated for this product. The latter tosylate salts are characterized by melting point (DSC) and purity (HPLC) and from these measurements one can not conclude to the base:acid ratio.

9
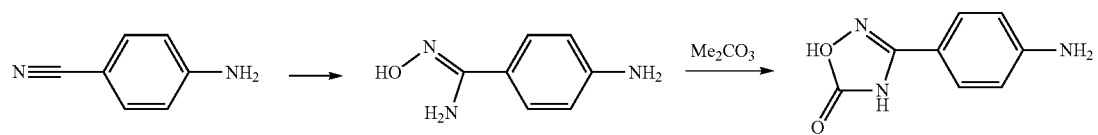
10
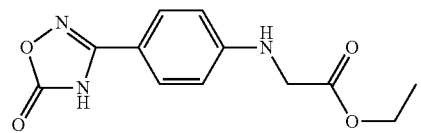
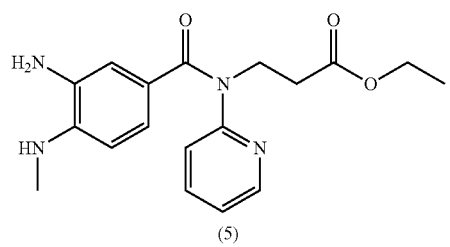
(5)
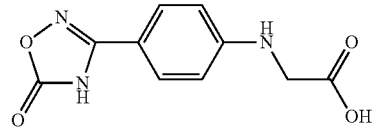
(7)
1.) CDI/THF
2.) AcOH, RT
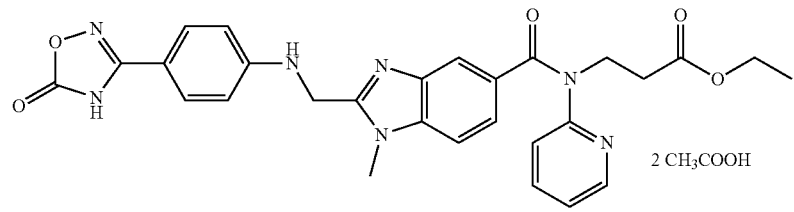
(8) * 2 AcOH
1.) Pd/H₂
2.) p-TsOH
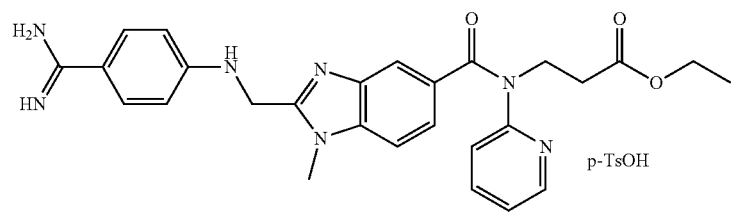
(2)*p-TsOH
acetone/H₂O
K₂CO₃
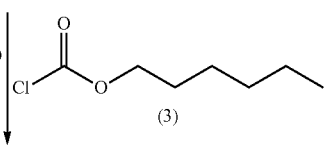
(3)

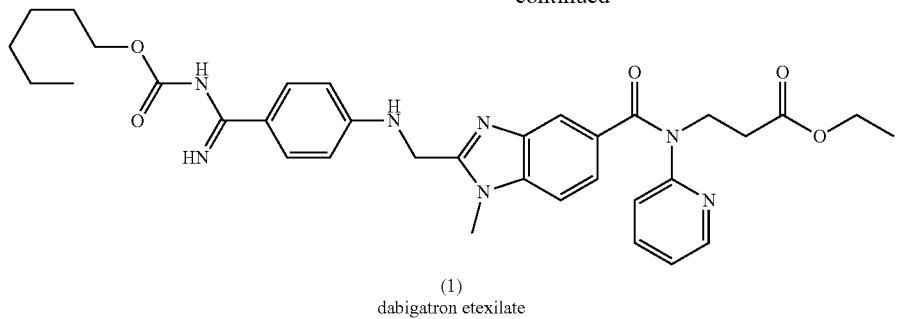

(1)
dabigatron etexilate

The new synthesis route of dabigatran etexilate according to WO 2006/000353 is shown on reaction scheme 3.

According to WO 2006/000353 dabigatran etexilate (1) is prepared as described in Examples 5A and 5B by reacting the tosylate salt ($2^x$p-TsOH) and hexyl chloro formiate (3) in an acetone-aqueous medium. The product dried at 45° C. is not characterized by any analytical data. On the basis of the calculations the product is presumed to be anhydrous.

The diacetate structure (8) of the starting material of the hydrogenation (polyvalent base) shows that the product formed (2) will also be capable of binding more than one acids. This is substantiated by a subsequent patent application (WO 2010/045900, reaction sequence 7, $2^x$2HCl).

On repeating the experiments in our laboratory in accordance with examples 4A, 4B and 4C we obtained tosylate salts of non-stoichiometrical composition. In the latter case the base:acid ratio was 1:(1.6-1.8) and this is in conformity with the fact that in said examples p-toluenesulfonic acid monohydrate was used in a 1.6-fold excess. For this reason the actual yield of the process ($8^x$2AcOH to $2^x$1.8p-TsOH) is significantly lower than that given in said international patent application.

According to WO 2006/000353 dabigatran etexilate (1) is prepared by crystallization from an acetone/water system (see/Example 5A) and in said process no drying agent or other dehydrating agent is used.

In a later International application (WO 2006/131491, Example 3) originator described the tetrahydrate form dabigatran etexilate (1) which was prepared by carrying out crystallization from an acetone-water mixture as well. Thus it is highly probable that the precipitation of the anhydrous base from an acetone-water mixture or from another water-containing mixture is not at all likely and can not be expected with a reasonable possibility.

We have also repeated Example 5A of WO 2006/000353 and failed to obtain anhydrous dabigatran etexilate (1) but rather the modification thereof containing four moles of water. The correction of the molecular weight to the water containing base results in a lower yield for this process too ($2^x$p-TsOH→$1^x$4H$_2$O).

The three modifications of the dabigatran etexilate (1) base—two anhydrous and the tetrahydro form—are described by Hauel et al in WO2006/131491. In this international patent application no process is disclosed for the preparation of 1 but reference is made rather to the basic patent. For this reason said new forms are obtained by recrystallization of a modification of unknowns structure from ethyl acetate (anhydrous form I and anhydrous form II; Examples 1 and 2) and a mixture of acetone and water (tetrahydrate form, Example 3), respectively.

In WO 2007/1742 one-pot procedures are protected by combining two different steps each described in earlier WO 2006/000353. The steps of the process are shown on reaction scheme 4. In one of said reaction routes dabigatran ethexylate (1) base is prepared by hydrogenating the intermediate ($8^x$2AcOH) containing the oxadiazole ring rather than by preparing the tosylate salt of the benzamidine derivative (2). The catalyst is filtered off and acylation is carried out in a mixture of acetone and water at 15° C. without isolating the reduced product (2). The dabigatran etexilate (1) base is not characterized but the calculations are related to the anhydrous form. The base (1) is converted into the mesylate salt ($1^x$MsOH) by reacting with methanesulfonic acid. According to Example 7 in the base synthesis the product (1) is recovered from a mixture of acetone and water without including a dehydrating step. Taking into consideration Example 3 of WO 2006/131491 the formation of the anhydrous product can not be expected. The yield corrected to the molecular weight of dabigatran etexilate (1) tetrahydrate is decreased in this case as well. ($8^x$2AcOH→$1^x$4H$_2$O).

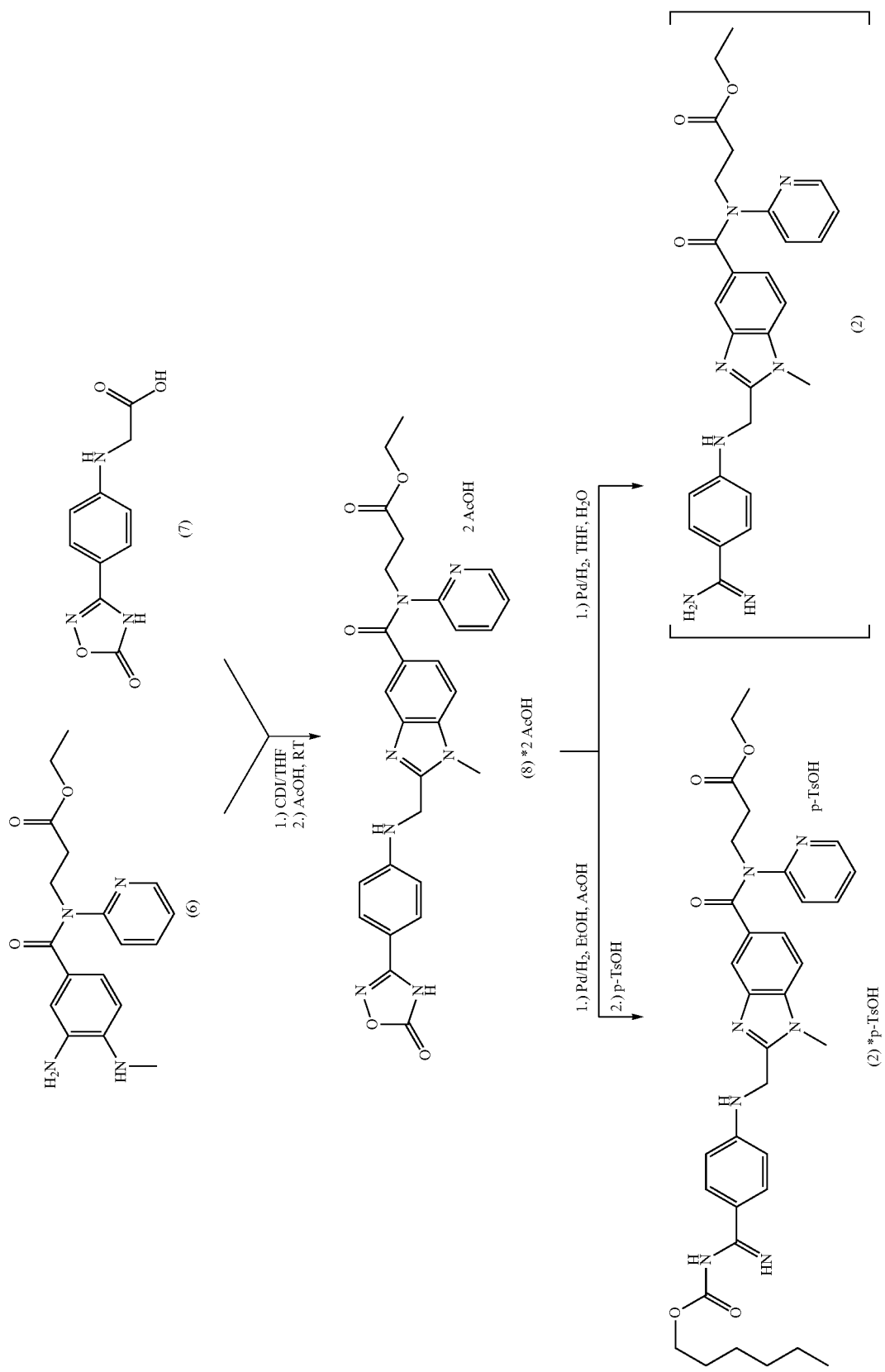

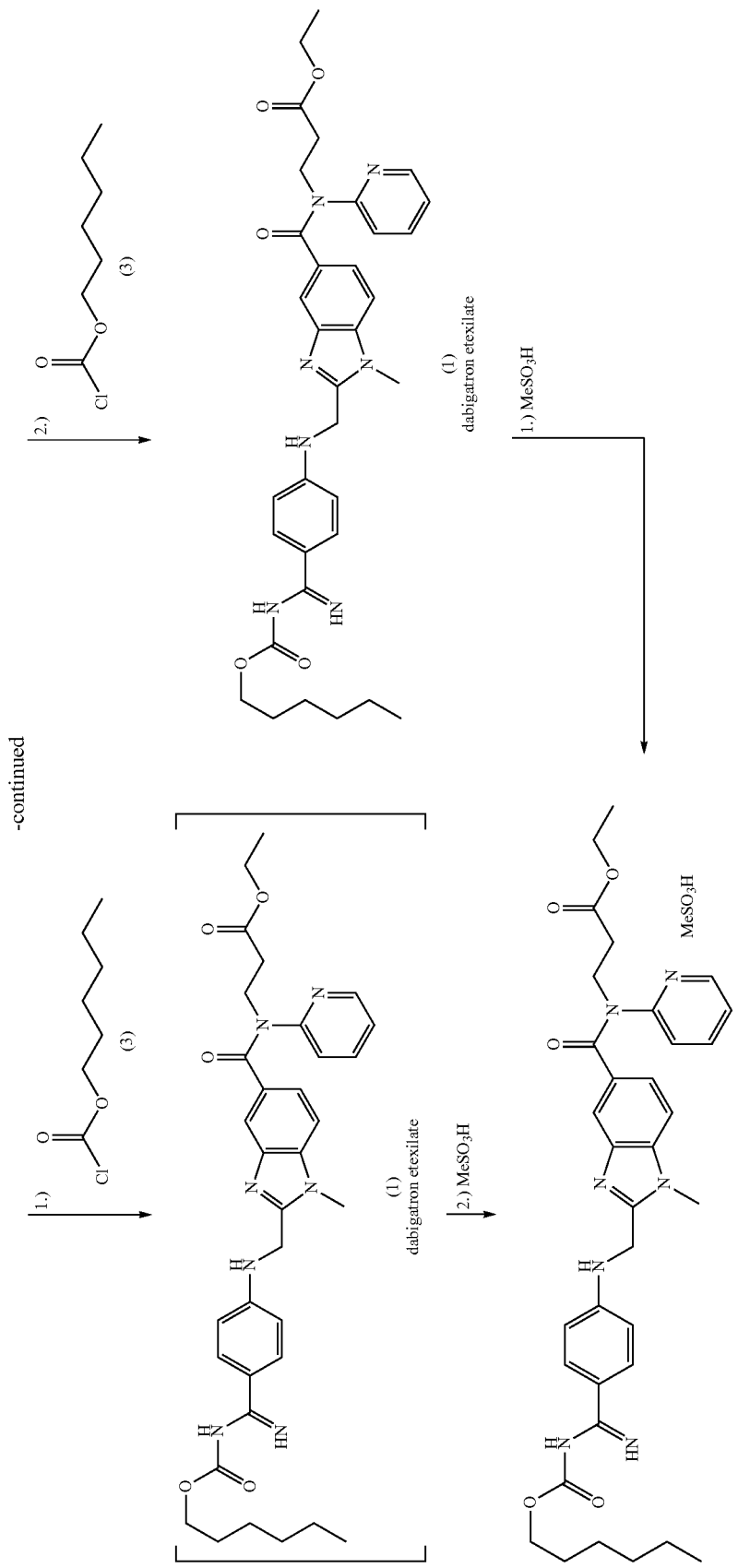

The synthesis routes of dabigatran etexilate (1) according to WO 2007/071742 are shown on reaction scheme 4.

In WO 2007/007142 three further variants are disclosed for the preparation of dabigatran etexilate (1) starting from the tosylate salt of the amidine (2); said procedures differ from each other in the reaction conditions and the method of working up. Thus Example 6A is identical with Example 5A of WO 2006/000353, however in the working up method of new variants 6B and 6C an azeotropic distillation is applied dehydration step. Accordingly in these cases actually the anhydrate of dabigatran etexilate (1) is formed and consequently the yield is lower (2*p-TsOH→1).

According to an other process of WO 2007/071742 (reaction scheme 4) the benzamidine derivative (2) is obtained after hydrogenation in the form of the tosylate salt, whereupon the dabigatran etexilate (1) formed in course of the acylation is not isolated from the reaction mixture but is used in the one-pot synthesis to yield the mesylate salt ($1^X$MsOH). In this case the tosylate salt of the amidine (2) is not characterized either but in the calculations it is presumed to be the monotosylate. On the basis of the indicated values the mesylate salt of the end-product (1) is obtained with a total yield of 79-81%, starting from the coupled oxadiazolone ($8^X$2AcOH) derivative ($8^X$2AcOH→$1^X$MsOH). The purity of the product is 99%.

Thus according to the reaction variant described in WO/2007/071742 the mesylate salt of the end-product (1) is prepared with a lower total yield when starting from the coupled oxadiazolone derivative (8*2AcOH→1*MsOH). A further significant drawback of the process is that no purification step is used during the preparation of the mesylate salt of the end-product (1). The indicated HPLC purity (>99%) is per se insufficient to meet the strong purity requirements of internationally accepted ICH Directives defined for pharmaceutical active ingredients by pharmaceutical monograph. Accordingly the amount of identified impurities can not exceed 0.15% and that of the unidentified impurities 0.10%. The HPLC method provides no information about the possible inorganic impurities of the active ingredient. The latter phenomenon can easily appear in course of crystallization by precipitation following the combination of several steps. A further disadvantage resides in the fact that while several methods are disclosed for the recrystallization (purification) of the base (1) (see WO 2006/000353, Example 5A; WO 2005/028468 Example 1-5), no procedures are known for the recrystallization of the mesylate salt of the end product (1*MsOH). Since the reliable fulfilment of the above criteria requires the insertion of at least purification step/s/into the manufacturing procedure, the above process is unable to guarantee the purity of the end product.

WO 2007/0718743 is practically an extension of WO 2007/071742; on carrying out the one pot synthesis route from the components of the coupling step (5,7) via the crude product of the hydrogenation (8*2AcOH), the process is continued as far as the mesylate salt of dabigatran etexilate (1). The HPLC purity (higher than 99%) of the product of the process (5→1*MsOH) is per se insufficient to comply with the severe purity requirements of pharamacopoeia. The process fails to use a purification step and this is a drawback. On combining more steps the risk of the appearance of contaminating impurities is significantly increased and said impurities can in optimal cases be removed from the active ingredient by means of recrystallization. In said process the end product is obtained by combining three steps but without including a purification step; according to our best knowledge the final recrystallization step is not settled yet and therefore the quality of the ends product can not be warranted.

A new variant of the extended basic patent (reaction scheme 2) is disclosed in WO 2009/111997. (reaction scheme 5). The preparation of the diamine derivative (5) is not carried out by catalytic hydrogenation of the nitro derivative (6), reaction scheme 2) but by sodium dithionite reduction of the hydrochloride salt of the nitro derivative (6*HCl). The compound (5) is coupled to the benzimidazole derivative (4) by known methods. Said intermediate is converted into the oxalate salt (4*(COOH)$_2$). In accordance with the basic patent the further steps of the synthesis of dabigatran etexilate (1) start from said oxalate salt. However these steps are not supported by examples and therefore no yields are known.

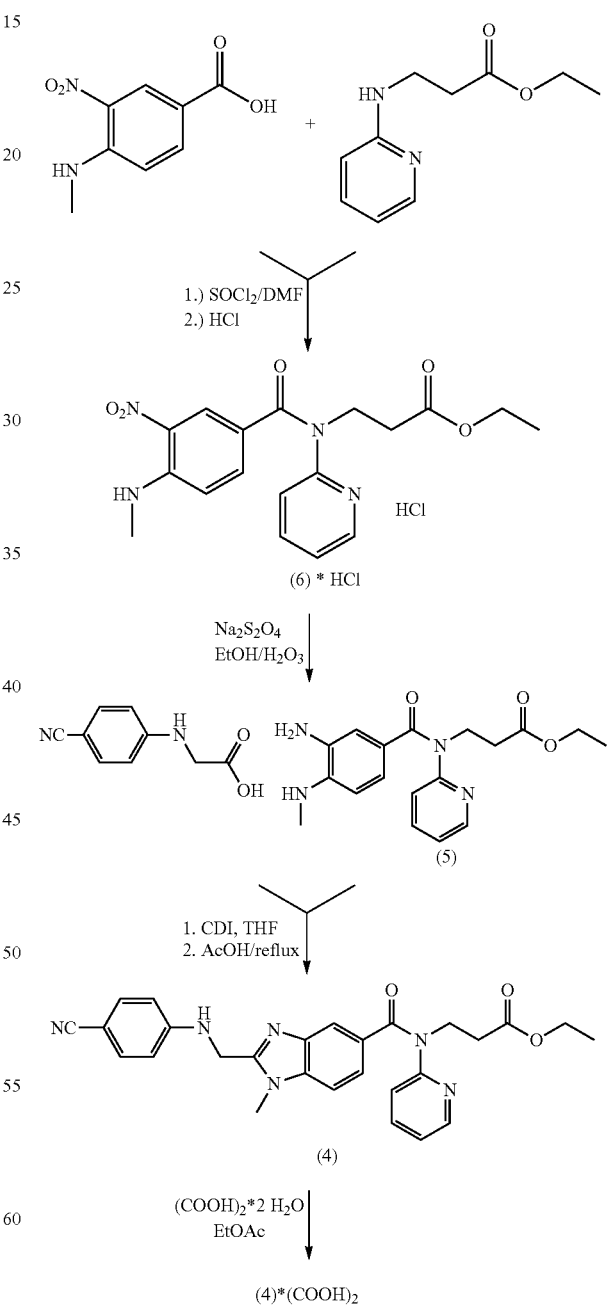

Reaction variant 5: Synthesis route of the intermediates of dabigatran etexilate (1) according to WO 2009/111997.

Taking into consideration the process of the originator described in WO 2006/000353 said reaction route according to WO 2009/111997 can not be regarded as economical Also in WO 2009/153214 a modified variant of the extended basic patent synthesis (reaction variant 2) is set forth. In this WO an improved process is reported for the reduction of the methylamino-nitro derivative (6). On performing the catalytic reduction of the nitro group both the utilization of the catalyst and the yield of the product (5) are improved.

In WO 2009/153215 a further one-pot embodiment of the synthesis route according to reaction scheme is disclosed. Thus the tosylate salt of the amidine (2) is prepared in a one-pot process starting from the phase products (5,7) obtained before the coupling step (reaction scheme 6). After the coupling reaction the non-isolated oxadiazole derivative (89 obtained is hydrogenated in the presence of ammonia and p-toluenesulfonic acid to yield the desired tosylate salt (5→2*p-TsOH). The tosylate salt formed is only characterized by HPLC data and the calculations infer a monotosylate structure.

Reaction scheme 6: Synthesis route of the intermediate of dabigatran etexilate (1) according to WO 2009/153215

An article published in 2009 (UP. Com. Journal 2009, 9, 20) reports a detailed process for the realization of the Pinner-reaction mentioned in the basic patent. Hydrolysis of the nitrile derivative (4) is carried out at room temperature with the aid of an approximately 100 molar amount of hydrochloric acid. Thus the end product (2*HCl) is obtained in an appropriate purity by five recrystallization steps. The hydrochloride of the amidine product (2) is characterized only by X-ray powder diagram. The low yield, the high dilution ratio and the difficulties of the purification step make said process unsuitable for industrial scale manufacture.

WO 2010/045900 provides a discussion of the modified basic patent route (reaction scheme 2). This international patent publication is essentially a continuation of an earlier international patent application of the authors (WO 2009/111997, reaction scheme 5). According to reaction scheme 7 the inventors started from the oxalate salt of the nitrile compound (4) and prepared the dabigatran etexilate (1) base via two new intermediate salt forms (monohydrochloride ethanolate and dihydrochloride) of the amidine (2).

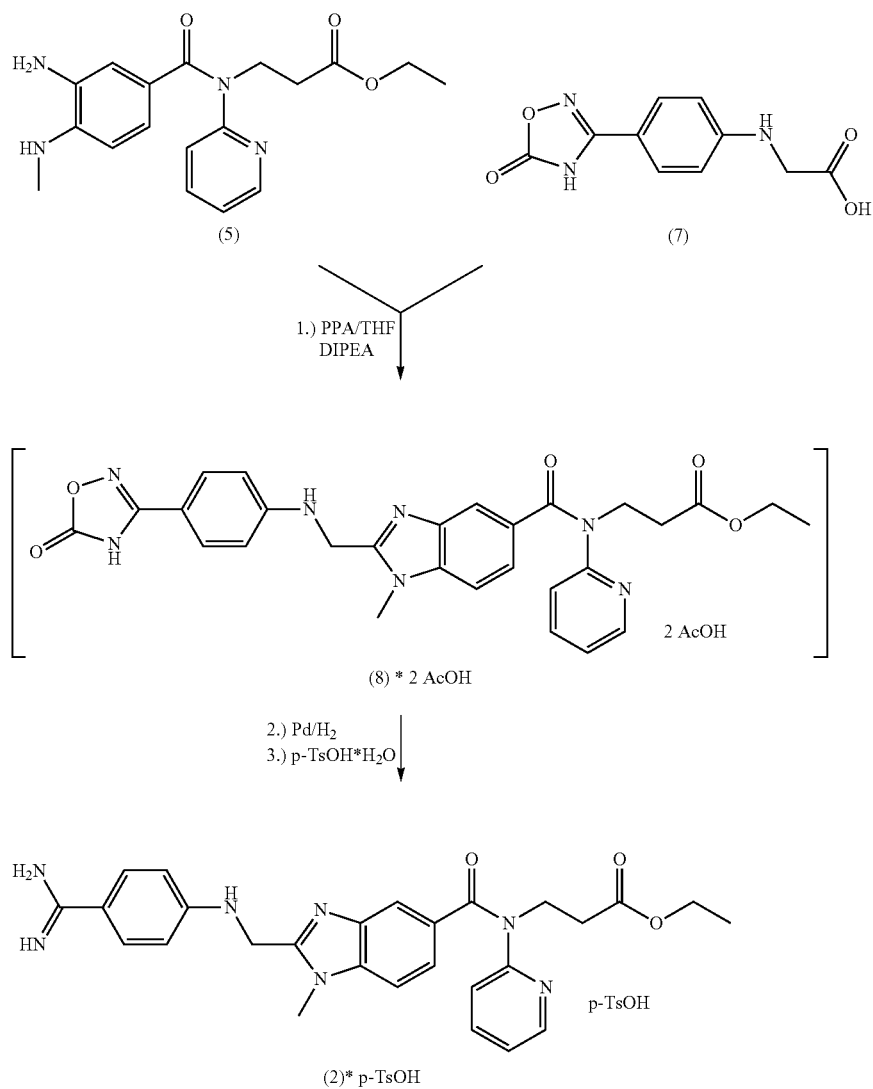

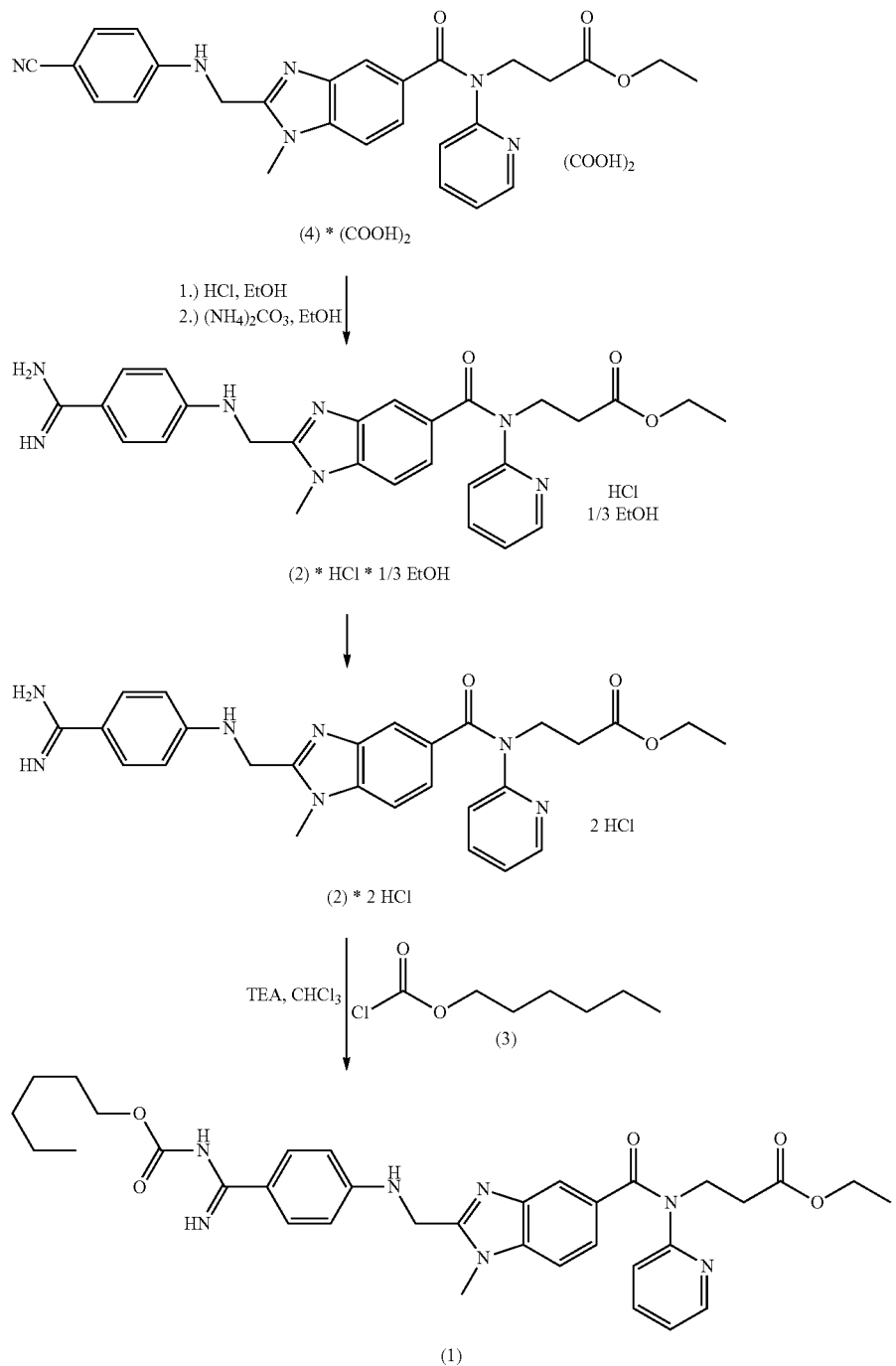

Reaction scheme 7: Synthesis route of dabigatran etexilate (1) according to WO 2010/0459000

The base (1) is prepared with low yield by a process starting from the diamine (5) derivative and completed by the reaction sequence shown on reaction schema 5 and 7. This process is not economical.

OBJECT OF THE INVENTION

Object of the present invention is the elaboration of a new synthetic process, which is more economical than the known procedures, can be carried out via crystalline intermediates easy to purify and is suitable for industrial scale manufacture.

The above object is achieved by means of the new manufacturing process of the present invention. The intermediate of the Formula (5) of one line of reaction sequence 8 is known from prior art. Intermediate compounds of the Formulae (9), (10), (11) and (12) appearing on the Y-line of the synthesis illustrated on reaction scheme 8 are known from prior art or can be prepared by analogous methods of the procedures disclosed in literature.

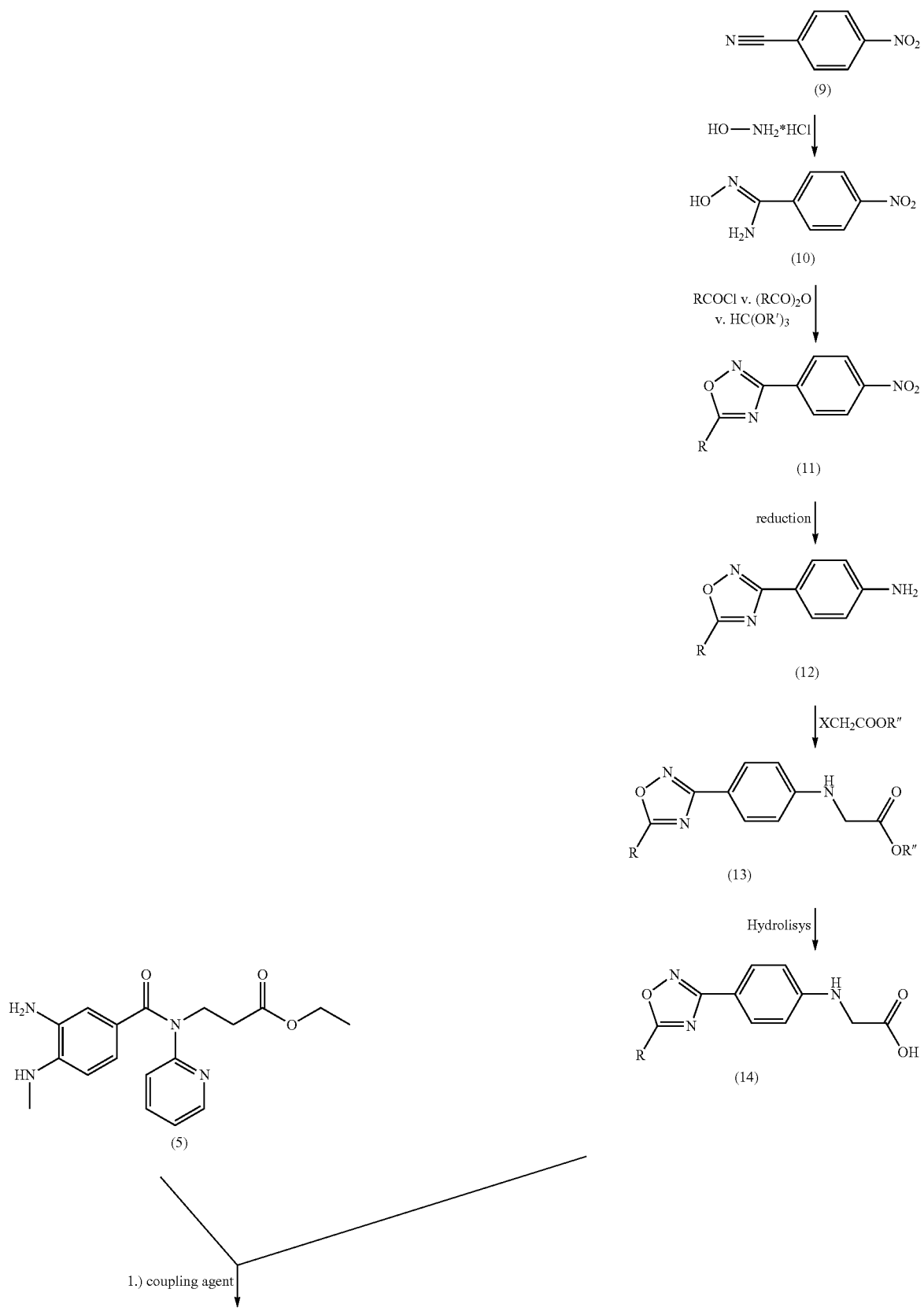

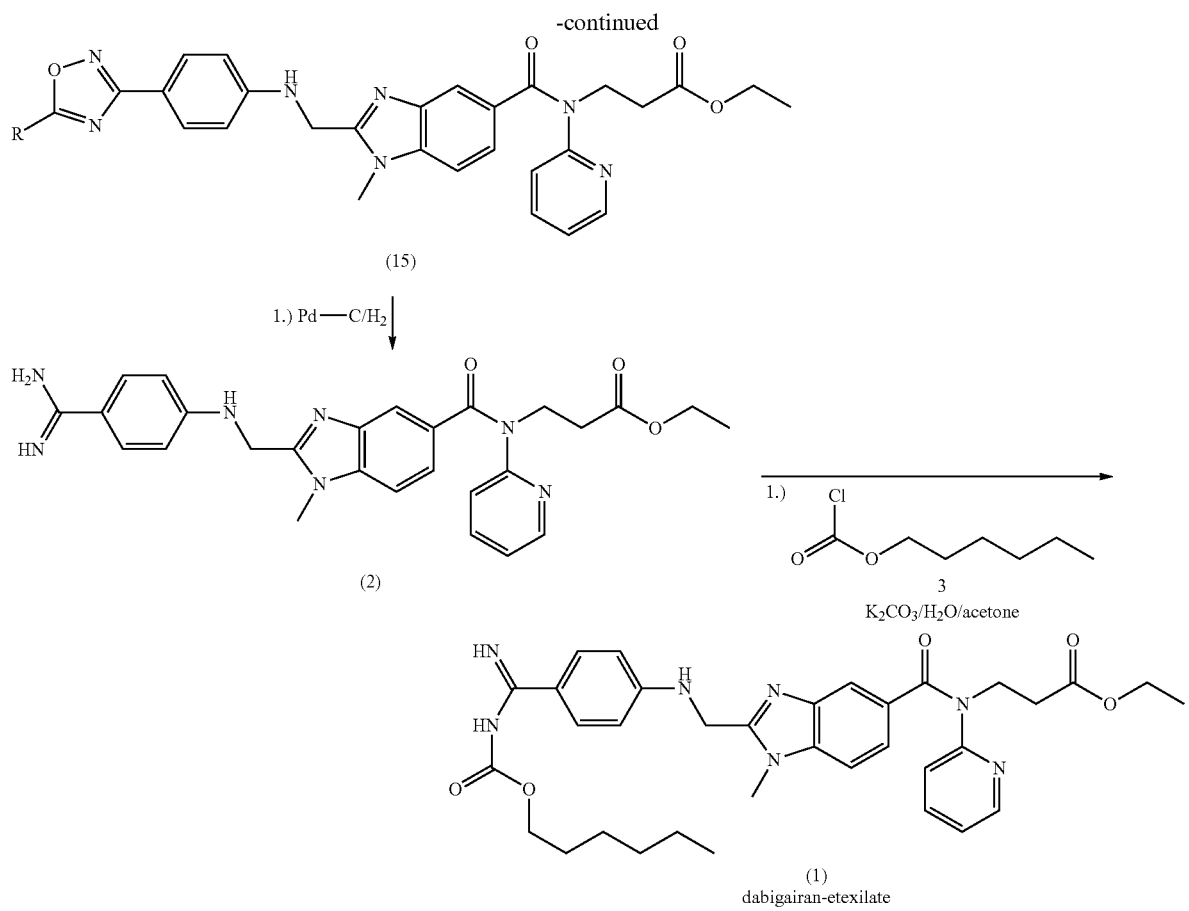

(1) dabigairan-etexilate

R = H₃ C₁-C₆alkil, aril, MOM, CF₃
R' = Me, Et
R" = C₁-C₆-alkil, aril
X = Cl, Br, I Reaction scheme 8: new synthesis route of dabigatran etexilate (1) according to the present invention.

The compounds of the Formulae (14) and (15) are not known from prior art.

The compounds of the Formulae (13), (14) and (15) are susceptible to salt formation and can exist in the form of hydrates and other solvates. The invention also relates to the salts, hydrates and solvates of the compounds of the Formulae (13), (14) and (15).

It has been surprisingly found that the process of the present invention shown on reaction scheme 8 is more efficient and economical than the procedures known from prior art for the preparation of the dabigatran etexilate base of the Formula (1).

It has also been found in a surprising manner that according to the present invention a well-characterized anhydrous product (1) of high purity is obtained via highly pure well-characterized intermediates easy to purify by means of an industrial scale manufacturing process. Particularly advantageous intermediates are the following compounds: the compound of the Formula 15 and the ditosylate salt (2)*2p-TsOH of the amidine (2) known from prior art.

According to the present invention there are also provided compounds of the general Formula 13 and salts thereof/ wherein R stands for hydrogen, $C_{1-6}$ straight or branched chain, saturated or partially or completely unsaturated hydrocarbon chain, $C_{1-6}$ straight or branched chain, partially or completely halogenated alkyl aryl or methoxy and R" represents $C_{1-6}$ straight or branched chain, saturated or partially or completely unsaturated hydrocarbon chain or $C_{1-6}$ straight or branched chain, partially or completely halogenated alkyl or aralkyl.

The invention also relates to a process for the preparation of compounds of the general Formula (13) and salts thereof starting from the compounds of the general Formula (12) or salts thereof/whereby in said general Formulae (12) and (13) R" and R are as stated above/.

The present invention also relates to compounds of the general Formula (14) and salts thereof (wherein R is as stated above).

The present invention also relates to a process for the preparation of compounds the general Formula (14) and salts thereof starting from compounds of the general Formula (13) (wherein R and R" are as stated above).

The present invention also relates to compounds of the general Formula/15/and salts thereof (wherein R and R" are as stated above).

The present invention also relates to a process for the preparation of compounds of the general Formula (15) and salts thereof starting from compounds of the general Formula (14) or salts thereof (wherein R has the same meaning as stated above).

The present invention also relates to the diacetate and tosylate salt of the compound of the Formula (2).

The invention also relates to the preparation of the compound of the Formula (2) or a salt thereof starting from compounds of the general Formula (15) or salts thereof (wherein R is as stated above).

The invention also relates to a process for the preparation of dabigatran etexilate of the Formula (1) or pharmaceutically acceptable salts thereof which comprises converting the compound of the Formula (2) or a salt thereof, preferably the diacetate or ditosylate salt of the compound of the Formula (2), particularly the ditosylate salt of the compound of the Formula (2)—obtained from the compounds of the general Formula (15) prepared according to the present invention—into the compound of the Formula (1) and thereafter into a pharmaceutically acceptable salt thereof.

DETAILED DESCRIPTION OF THE INVENTION

The inventors of EP 16212204 describe the preparation of the compounds in examples 22-26. The 4-nitrobenzonitrile (9, reaction scheme 8) is refluxed with hydroxylamine for 14 hours to give N'-hydroxy-4-nitro-benzene-carboximide-amide (10) with a yield of 88%. This compound is heated to boiling with acetic anhydride for 11 hours, the reaction mixture is worked up and after purification by chromatography the 5-methyl-3-(4-nitrophenyl)[1,2,4]oxadiazole compound (11, R is methyl) is obtained with a yield of 61%. On carrying ring-closure of (10) with orto formic acid triethyl ester in place of acetic anhydride the corresponding analogue (wherein R is hydrogen in place of methyl in the compound of the general Formula (11)), namely the 3-(4-nitrophenyl)[1,2,4]-oxadiazole is obtained. Reduction of the nitro derivatives (11, R stands for hydrogen or methyl) with elementary zinc in the presence of ammonium chloride yields the corresponding aniline derivative (12, R stands for hydrogen or methyl) with a yield of 95% or 94%, respectively.

The inventors of WO 2007/053094 reacted in reference example 25 4-nitro-benzonitrile (9) with hydroxylamine and obtained N'-hydroxyl-nitro-benzenecarboximide-amide (10) with a yield of 88% and in a purity of about 93%. Said compound was O-acylated with acetyl chloride in the presence of triethyl amine to yield (E)-Sacetoxy-4-nitro-benzimidamide, which was subjected to ring closure with tetrabutyl ammonium fluoride and to purification by flash chromatography. The 5-methyl-3-(4-nitrophenyl)[1,2,4]oxadiazole compound (11, R is methyl) thus obtained was subjected to reduction with elementary iron in glacial acetic acid to yield 4-(5-methyl[1,2,4]oxadiazole-3-yl)-aniline (12, R is methyl) in a purity of 92% with a yield of 96%, related to the ring-closure step. In said international patent publication also the analogous synthesis of the compounds of the general Formula 12 (wherein R is ethyl, isopropyl and methoxymethyl) is described (see reference examples 26-28).

The synthesis of said oxadiazole derivative (12, R is methyl) is described in the publication of Jin et al (Bioorg. Med. Chem. Lett. 2008, 18, 5481). The compound of the Formula 9 is reacted with hydroxylamine to yield the amidoxime of the Formula 10 which is reacted with acetyl chloride in pyridine to give the oxadiazole of the general Formula 11 (wherein R is methyl). The aromatic nitro group is reduced to give the corresponding aniline derivative (12, R is methyl). The publication does not disclose the yields of the steps.

The aminophenyl-oxadiazole type compounds of the general Formula 12 were prepared by procedures known from prior art.

In case of the compound of the general Formula 12 (wherein R is trifluoromethyl) the starting material of the general Formula 11 (wherein R is trifluoromethyl) was prepared according to the publication of Buscerni Silvestre et al (Eur. J. Org. Chem. 2004, 5, 974-980) whereby from said compound we formed the aniline derivative required (12, R is trifluoromethyl) according to the process known from EP 16122204.

The compounds of the general Formula (13) and salts thereof are prepared by reacting a compound of the general Formula (12) or a salt thereof with bromo ethyl acetate or chloro ethyl acetate, preferably with bromo ethyl acetate, in the presence of an acid binding agent. For this purpose an organic or inorganic base, preferably the Hunig base or methyl amine can be used.

The compounds of the general Formula (14) and salts thereof are prepared from the compounds of the general Formula (13) or salts thereof. Ester hydrolysis is carried out under acidic or alkaline conditions, preferably under alkaline conditions, particularly by using an alkali hydroxide. The reaction takes place almost quantitatively (yield 97%).

The preparation of the compounds of the general Formula (15) starts from the compounds of the general Formula (14) or salts thereof whereby the coupling and ring-closure reactions are preferably carried out in a one-pot process. The reaction is preferably carried out in the presence of an acylation promoter, particularly 1,1'-carbonyl-diimidazole (CDI) or propyl-phosphonic anhydride (T3P).

The compound of the Formula (2) is prepared from the compounds of the general Formula (15) or salts thereof. The opening of the oxadiazole ring is performed by catalytic hydrogenation in the presence or absence of an acid, optionally with a mixture of an acid and a metal, particularly by hydrogenation on a palladium-charcoal catalyst. The amidine of the Formula (2) formed can be separated in form of a salt. As acid for salt formation preferably hydrochloric acid, acetic acid, p-toluenesulfonic acid or oxalic acid can be used, in a 1-3 molar amount. One can particularly advantageously use p-toluenesulfonic acid in an amount of 2 moles.

The invention also relates to a process for the preparation of anhydrous dabigatran etexilate of the Formula (1) starting from a salt of the compound of the Formula (2)—whereby the acid part of the salt may be preferably acetic acid or p-toluenesulfonic acid in a 2-3 molar equivalent amount or oxalic acid in a 1 molar equivalent amount, particularly advantageously p-toluenesulfonic acid in a 2 molar equivalent amount.

It has been found that the new process of the present invention, which is carried out via new intermediates, is more suitable for industrial scale manufacture than the procedures known from prior art. The intermediates of the invention process are unambiguously defined, well characterized compounds which have high melting point, easily crystallize and guarantee the desired quality of the pharmaceutical active ingredient.

The aforesaid particularly applies to the key intermediates of the reaction route of the invention—namely the compounds of the general Formula (15)—which contrary to other similar technologies, are intermediates stable, possess excellent solubility parameters and can be readily purified not only in the form of salts formed with acids but also as the base.

It has also been found in a surprising manner that although the monotosylate salt of the compound of the Formula (2) was known from prior art, the stochiometry of the salt prepared according to the present patent application corresponds to a 1:2 ratio. Accordingly the ditosylate salt of the compound of the Formula (2) is formed which can be used for the preparation of dabigatran etexilate (1) as an intermediate more favourably than the monotosylates salt or other salts of the compound of the Formula (2). The ditosylate of the compound of the Formula (2)—similarly to the corresponding dihydrochloride (reaction scheme 7, 2*2HCl)—possesses more advantageous crystallization properties than the corresponding salts which contain only one acid (base(2):acid=1:1). Additionally the knowledge of the exact stoichiometrical composition of the tosylate salt is a fundamental prerequisite for the calculation of the reaction parameters of the next step or for the determination of the production parameters of the formed product (1), respectively.

The invention also relates to a pharmaceutical composition comprising as active ingredient a therapeutically effective amount of dabigatran etexilate (1) prepared as described above or a pharmaceutically acceptable salt thereof in admixture with one or more pharmaceutically acceptable auxiliary agent/s/.

The invention also relates to the use of said pharmaceutical compositions for the prevention of post operate deep venous thrombosis and cerebral haemorrhage.

The invention also relates to the use of the active ingredient dabigatran etexilate (1) prepared as described above or a pharmaceutically acceptable salt thereof for the preparation of pharmaceutical compositions suitable for the treatment or prevention of post operative deep venous thrombosis and cerebral haemorrhage.

Further details of the present invention are to be found in the following Examples without limiting the scope of protection to said Examples.

EXAMPLES

Example 1

Preparation of ethyl-N-[4-(5-methyl-1,2,4-oxadiazole-3-yl)-phenyl]-glycinate (13, R is methyl and R''' is ethyl)

Into a 1000 ml round-bottomed flask 22.0 g (125.6 nillimoles) of 4-(5-methyl-1,2,4-oxadiazole-3-yl)-aniline (12, R is methyl), 220 ml of toluene and 25.4 g (251.1 millimoles) of triethyl amine are weighed in whereupon to the suspension a solution of 31.4 g (188.4 millimoles) of bromo ethyl acetate in 44 ml of toluene are added. After the addition of 110 mg (0.7 millimoles) of a potassium iodide catalyst the reaction mixture is heated to boiling and stirred at this temperature for 24 hours. The reaction having been completed the mixture is concentrated, to the residue cyclohexane is added and crystallization is carried out at 0-5° C. The precipitated crude product is washed with cyclohexane and water and dried in vacuo to constant weight. Thus 27.2 g (83%) of the title compound are obtained. The analytical purity sample is obtained after recrystallizatrion, mp.: 111-116° C.

IR (KBr): 3412, 1733, 1614, 1376, 1213 cm$^{-1}$.

$^1$H NMR (DMSO-d$_6$, 500 MHz): δ=7.72 (~d, J=8.8 Hz, 2H), 6.67 (~d, J=8.8 Hz, 2H), 4.13 (q, J=7.1 Hz, 2H), 3.98 (d, J=6.4 Hz, 2H), 2.60 (s, 3H), 1.21 (t, J=7.1 Hz, 3H) ppm.

Example 2

Preparation of ethyl-N-[4-(5-methoxymethyl-1,2,4-oxadiazole-3-yl)-phenyl]-glycinate (13, R is methoxymethyl and R'' is ethyl)

Into a 50 ml round-bottomed flask 1.1 g (5.4 millimoles) of 4-/5-methoxymethyl-1,2,4-oxadiazole 3-yl/-aniline (12, R is methoxymethyl/, 11 ml of toluene and 1.1 g (11 millimoles) of triethyl amine are added. To the suspension thus obtained a solution of 1.3 g (8 millimoles) of bromo ethyl acetate in 3 ml of toluene is added. After addition of 10 mg (0.07 millimoles) of a potassium iodide catalyst the reaction mixture is heated to boiling and stirred at this temperature for 24 hours. The reaction having been completed the mixture is evaporated, to the residue cyclohexane is added and crystallization is performed at 0-5° C. to constant weight. The crude product is filtered, washed with water and dried in vacuo to constant weight. Thus 1.5o g (94%) of the title compound are obtained. The analytical sample is obtained after recrystallization. Mp.) 75-79° C.

IR (KBr): 3415, 1733, 1617, 1360, 1212 cm$^{-1}$.

$^1$H NMR (DMSO-d$_6$, 400 MHz): δ=7.74 (~d, J=8.7 Hz, 2H), 6.68 (~d, J=8.8 Hz, 2H), 4.76 (s, 2H), 4.13 (q, J=7.1 Hz, 2H), 3.98 (d, J=6.4 Hz, 2H), 3.41 (s, 3H), 1.20 (t, J=7.1 Hz, 3H) ppm.

Example 3

Preparation of N-[4-(5-methyl-1,2,4-oxadiazol-3-yl)-phenyl]-glycine (14, R is methyl)

Into a 250 ml round-bottomed flask 55.0 g (19.1 millimoles) of N-[4-(5-methyl-1,2,4-oxadiazol-3-yl)-phenyl]-glycinate (13, R is methyl) and 100 ml of a 5 vol % sodium hydroxide solution (125 millimoles) are weighed in. The suspension obtained is stirred at room temperature for 16-20 hours. The solution obtained is cooled and the pH is adjusted to 5 with a 1:1 diluted mixture of concentrated hydrochloric acid and water. The precipitate is filtered, washed with water and dried in vacuo to constant weight. Thus 4.30 g of the title compound are obtained (97%). Mp.: 178-181° C.

IR (KBr): 3409, 1718, 1614, 1596, 1363, 1186 cm$^{-1}$.

$^1$H NMR (DMSO-d$_6$, 500 MHz): δ=12.62 (br s, 1H), 7.72 (d, J=8.8 Hz, 2H), 6.68 (d, J=8.8 Hz, 2H), 6.51 (br, 1H), 3.89 (s, 2H), 2.59 (s, 3H) ppm.

Example 4

Preparation of N-[4-(5-mrethoxymethyl-1,2,4-oxadiazol-3-yl)-phenyl]-glycinate (14, R is methoxymethyl)

Into a 25 ml round-bottomed flask 0.50 g (1.7 millimoles) of ethyl-N-[4-(5-methoxymethyl-1,2,4-oxadiazol-3-yl)-phenyl]-glycinate (13, R is methoxymethyl) and 10 ml of a 5 vol. % (12.5 millimoles) sodium hydroxide solution are weighed in. The suspension obtained is stirred at room temperature for 16-20 hours. The solution obtained is cooled and the pH is adjusted to 2 with a 1:1 dilution of concentrated hydrochloric acid and water. The precipitate is filtered, washed with water and dried in vacuo to constant weight. Thus 0.30 g/69%/of the title compound are obtained. The analytical sample is obtained after recrystallization, mp.: 152-155° C.

IR (KBr): 3382, 1726, 1612, 1482, 1433, 1348 cm$^{-1}$.

$^1$H NMR (DMSO-d$_6$, 500 MHz): δ=1.44 (b, 1H), 7.75 (~d, J=8.6 Hz, 2H), 6.66 (~d, J=8.8 Hz, 2H), 6.55 (b, 1H), 4.76 (s, 2H), 3.89 (s, 2H), 3.42 (s, 3H) ppm.

Example 5

Preparation of ethyl-{[1-methyl-2-({[4-(5-methyl-1,2,4-oxadiazol-3-yl)-phenyl]-amino}-methyl)-1H-benzimidazole-5-yl]-carbonyl}-N-pyridine-2-yl-beta-alaninate (15, R is methyl)

Into a 1000 ml round-bottomed flask 29.4 g (85.8 millimoles) of ethyl-N-{[3-amino-4-methylamino-phenyl]-carbonyl}-N-pyridine-2-yl-beta-alaninate (5) and 160 ml of ethyl acetate are weighed in whereupon to the suspension at room temperature under stirring 20.0 g (85.8 millimoles) of N-[4-(5-methyl-1,2,4-oxadiazol-3-yl)-phenyl]-glycine (14, R is methyl) are added. To the suspension in portions a 25 vol. % solution of 51.3 g (161 millimoles) of propyl-phosphonic anhydride in ethyl acetate is added while the reaction mixture is warmed to 50-55° C. The reaction mixture is stirred at 50-55° C. for a further period of 2 hours. The reaction having been completed the solution is concentrated, the residue is cooled to 15° C. and the pH is adjusted to 7-8 with a potassium hydrogen carbonate solution. The precipitate is filtered, washed with water and ethyl acetate and dried in vacuo to constant weight. Thus 41.6 g (90%) of the title compound are obtained. The analytical sample is obtained after recrystallization. Mp.: 173-176° C.

IR (KBr): 3400, 1729, 1639, 1471, 1338 cm$^{-1}$.

$^1$H NMR (DMSO-d$_6$, 400 MHz): δ=8.38 (m, 1H), 7.72 (d, J=8.7 Hz, 2H), 7.54 (m, 1H), 7.48 (d, J=1.1 Hz, 1H), 7.40 (d, J=8.4 Hz, 1H), 7.18 (dd, J$_1$=1.5 Hz, J$_2$=8.4 Hz, 1H), 7.12 (m, 1H), 6.90 (m, 1H), 6.86 (b, 1H), 6.88 (d, J=8.8 Hz, 2H), 4.59 (d, J=5.5 Hz, 1H), 4.24 (t, J=7.1 Hz, 2H), 3.98 (q, J=7.1 Hz, 2H), 3.78 (s, 3H), 2.70 (t, J=7.1 Hz, 2H), 2.59 (s, 3H), 1.12 (t, J=7.1 Hz, 3H) ppm.

Example 6

Preparation of ethyl-N-{[1-methyl-2-({[4-(5-methoxymethyl-1,2,4-oxadiazol-3-yl)-phenyl]-amino}methyl)-1H-benzimidazole-5-yl]-carbonyl}-N-pyridine-2-yl-β-alaninate (15, R is methoxymethyl)

Into a 50 ml round bottomed flask 0.25 g (0.9 millimole) of N-[4-(5-methoxymethyl-1,2,4-oxadiazol-3-yl)-phenyl]glycine (14, R is methoxymethyl), 0.31 g (0.9 millimoles) of ethyl-N-{[3-amino-4-methylamino-phenyl-carbonyl}-N-pyridine-2-yl-β-alaninate (5) and 3 ml of ethyl acetate are added. To the suspension obtained a 25% ethyl acetate solution of 0.68 g (2.1 millimoles) of propyl phosphonic anhydride (T3P) is added at room temperature under stirring. The reaction mixture is warmed to 50° C. and stirred at this temperature for a further 2 hours. The reaction having been completed the solution is concentrated, cooled to 15° C. and the pH is adjusted to 7-8 with the aid of a potassium hydrogen carbonate solution. The precipitate is filtered, washed with water and ethyl acetate and dried in vacuo to constant weight. Thus 0.27 g (51%) of the title compound is obtained. The analytical sample is obtained after recrystallization. Mp.: 145-150° C.

IR (KBr): 3400, 1732, 1652, 1615, 1468 cm$^{-1}$.

$^1$H NMR (DMSO-d$_6$, 400 MHz): δ=8.39 (m, 1H), 7.74 (~d, J=8.5 Hz, 2H), 7.54 (m, 1H), 7.48 (s, 1H), 7.40 d, J=8.4 Hz, 1H), 7.18 (d, J=8.4 Hz, 1H), 7.11 (m, 1H), 6.90 (m, 1H), 6.89 (b, 1H), 6.88 (~d, 2H), 4.76 (s, 2H), 4.60 (d, J=5.2 Hz, 2H), 4.23 (t, J=7.0 Hz, 2H), 3.98 (q, J=7.0 Hz, 2H), 3.78 (s, 3H), 3.41 (s, 3H), 2.69 (t, J=7.0 Hz, 2H), 1.12 (t, J=7.1 Hz, 3H) ppm.

Example 7

Preparation of the 1:1 oxalate salt of the ethyl-N-{[1-methyl-2-({[4-(5-methyl-1,2,4-oxadiazol-3-yl)phenyl]amino}methyl)-1H-benzimidazole-5-yl]-carbonyl}-N-pyridine-2-yl-β-alaninate (15, R is methyl)

Into a 50 ml round-bottomed flask 1.0 g (4.3 millimoles) of N-[4-(5-methyl-1,2,4-oxadiazol-3-yl)phenyl]glycine (14, R is methyl) and 1.47 g (4.3 millimoles) of ethyl-N-{[3-amino-4-methylamino)phenyl]carbonyl}-N-pyridine-2-yl-β-alaninate (5) and 8 ml of ethyl acetate are added. To the suspension a 25% ethyl acetate solution of 3.07 g (9.7 millimoles) of propyl phosphonic anhydride (T3P) is added at room temperature under stirring. The reaction mixture is warmed to 50° C. and is stirred at this temperature for a further 2 hours. The reaction having been completed the solution is cooled to 20-25° C., 25 ml of tetrahydrofurane are added and the mixture is washed with a potassium hydrogen carbonate solution and water. The solution is evaporated and dehydated with the aid of ethyl acetate. To the ethyl acetate suspension formed a solution of 0.39 g (4.3 millimoles) of oxalic acid and 4 ml of ethyl acetate is added. The precipitate is dried in vacuo to constant weight. Thus 1.62 g (60%) of the title compound are obtained. Mp.: 185-188° C.

IR: 3272, 1757, 1740, 1641, 1328 cm$^{-1}$.

$^1$H NMR (DMSO-d$_6$, 500 MHz): δ=8.39 (m, 1H), 7.72 (~d, J=8.6 Hz, 2H), 7.55 (m, 1H), 7.49 (s, 1H), 7.42 (d, J=8.4 Hz, 1H), 7.19 (d, J=8.2 Hz, 1H), 7.12 (m, 1H), 6.91 (m, 1H), 6.85 (~d, J=8.6 Hz, 2H), 4.61 (s, 2H), 4.23 (t, J=7.1 Hz, 2H), 3.98 (q, J=7.1 Hz, 2H), 3.79 (s, 3H), 2.69 (t, J=7.1 Hz, 2H), 2.59 (s, 3H), 1.12 (t, J=7.1 Hz, 3H).

Example 8

Preparation of the 1:2 acetic acid salt of ethyl-N-[(2-{[(4-carbamimidoylphenyl)-amino]methyl}-1-methyl-1H-benzimidazol-5-yl)-carbonyl]-N-pyridine-2-yl-β-alaninate (2)

Into a 250 ml round-bottomed pressure-tight steel reactor 2.0 g (3.7 millimoles) of ethyl-N-{[11-methyl-2-({[4-(5-methyl-1,2,4-oxadiazole-3-yl)phenyl]amino}-methyl)-1H-benzimidazole-5-yl]-carbonyl}-N-pyridine-2-yl-beta-alaninate (15, R is methyl), 30 ml of ethanol and 3 ml of acetic acid are weighed in, whereupon 200 mg of a 5% palladium-charcoal catalyst are added. After inertization the reaction mixture is hydrogenated at 50° C. under a pressure of 5 bar for 6 hours. The reaction mixture is filtered and the solvent is distilled off. The crude product is treated with ethyl acetate and cyclohexane and crystallized at 0-5° C. The product is filtered, washed with cyclohexane and dried in vacuo to constant weight.

Thus 1.51 g (66%) of the title compound are obtained. The analytical sample is obtained after recrystallization, mp 214-216° C.

IR (KBr): 3331, 2984, 1730, 1651, 1611, 1497, 1326 cm$^{-1}$.

$^1$H NMR (DMSO-d$_6$, 500 MHz): δ=11.1 (br s, 2H), 8.5 (b, 1H), 8.39 (m, 1H), 7.62 (d, J=8.8 Hz, 2H), 7.54 (m, 1H), 7.48 (d, J=1.1 Hz, 1H), 7.40 (d, J=8.4 Hz, 1H), 7.24 (t, J=5.0 Hz, 1H), 7.16 (dd, J=1.3 Hz, 1H), 7.12 (m, 1H), 6.90 (m, 1H), 6.85 (d, J=8.8 Hz, 2H), 4.63 (d, J=5.1 Hz, 2H), 4.23 (t, J=7.1 Hz, 2H), 3.98 (q, J=7.1 Hz, 2H), 3.77 (s, 3H), 2.69 (t, J=7.1 Hz, 2H), 1.86 (br, 6H), 1.12 (t, J=7.1 Hz, 3H) ppm.

Elementary analysis, calc (C$_{31}$H$_{37}$N$_7$O$_7$): C, 60.09; H, 6.02; N, 15.82; O, 18.07%. Found: C, 59.42; H, 6.15; N, 15.88; O, 18.55%.

Example 9

Preparation of the 1:2 p-toluenesulfonic acid salt of ethyl-N-[(2-{[(4-carbamimidoylphenyl)-amino]methyl}-1-methyl-1H-benzimidazole-5-yl)-carbonyl]-N-pyridine-2-yl-β-alaninate (29 from ethyl-N-{[1-methyl-2-({[4-(5-methyl-1,2,4-oxadiazol-3-yl)-phenyl]amino}methyl)-1H-benzimidazole-5-yl]-carbonyl}-N-pyridine-2-yl-β-alaninate (15, R is methyl)

Into a 850 ml pressure tight steel reactor 9.0 g (16.7 millimoles of ethyl-N-{[1-methyl-2-({[4-(5-methyl-1,2,4-oxadiazole-3-yl)phenyl]amino}methyl)-1H-benzimidazole-5-yl]-carbonyl}-N-pyridine-2-yl-β-alaninate (15, R is methyl), 135 ml of ethanol and 13.5 ml of acetic are weighed in whereupon 1.80 g of a 5% palladium-charcoal catalyst are added. After inertization the reaction mixture is hydrogenated at 50° C. under a pressure for 5 bar for 6 hours. The reaction mixture is filtered and the solvent is removed. The crude product is dissolved in 135 ml of ethyl acetate whereupon a solution of 5.71 g (30 millimoles, 1.8 equivalents) of p-toluenesulfonic acid monohydrate and 57 ml of ethyl acetate is added. The suspension is stirred first at room temperature and then crystallization is made complete at 0-5° C. The product is filtered, washed with some ethyl acetate and dried in vacuo to constant weight. Thus 10.87 g (77%) of the title compound are obtained. Mp.: 186-188° C.

IR (KBr): 3336, 3167, 1724, 1685, 1657, 1610, 1213, 1182, 1011 cm$^{-1}$.

HNMR (DMSO-d$_6$, 400 MHz): δ=8.92 (br s, 2H), 8.55 (br s, 2H), 8.36 (m, 1H), 7.77 (d, J=8.6 Hz, 1H), 7.68 (d, J=9.0 Hz, 2H), 7.61 (m, 1H), 7.59 (m, 1H), 7.49 (b, 1H), 7.49 (d, J=8.1 Hz, 2H), 7.39 (dd, J$_1$=1.5 Hz, J$_2$=8.6 Hz, 1H), 7.16 (m, 1H), 7.11 (d, J=7.9 Hz, 2H), 7.06 (m, 1H), 6.88 (d, J=9.0 Hz, 2H), 4.94 (s, 2H), 4.2 (t, J=7.0 Hz, 2H), 3.97 (q, J=7.1 Hz, 2H), 3.92 (s, 3H), 2.70 (t, J=7.0 Hz, 2H), 2.28 (s, 3H), 1.12 (t, J=7.0 Hz, 3H) ppm.

Elementary analysis: calc: C$_{41}$H$_{45}$N$_7$O$_9$S$_2$: C, 58.35; H, 5.81; N, 11.62; O, 17.06; S, 7.60%.

Found: C, 57.99; H, 5.38; N, 11.68; O, 17.27; S, 7.68%.

Example 10

Preparation of the 1:2 p-toluenesulfonic acid salt of ethyl-N-[(2-{[(4-carbamimidoylphenyl)amino]methyl}-1-methyl-1H-benzimidazole-5-yl)-carbonyl]-N-pyridine-2-yl/-β-alaninate (2) from ethyl-N-{[1-methyl-2-({[4-(5-methoxymethyl-1,2,4-oxadiazole-3-yl)phenyl]amino}methyl)-1H-benzimidazole-5-yl]-carbonyl}-N-pyridine-2-yl-β-alaninate (15, R is methoxymethyl)

Into a 80 ml pressure tight steel reactor 0.23 g (0.4 millimole) of ethyl N-{[1-methoxymethyl-2-({[4-(5-methyl-1,2,4-oxadiazole-3-yl)phenyl]amino}methyl)-1H-benzimidazole-5-yl]carbonyl}-N-pyridine-2-yl-β-alaninate (15, R is methoxymethyl), 4 ml of ethanol, 0.4 ml of acetic acid and thereafter 50 mg of a 5% palladium-charcoal catalyst are weighed in. After inertization the reaction mixture is hydrogenated at 50° C. under a pressure of 5 bar for 6 hours. The reaction mixture is filtered and the solvent is removed. The crude product is dissolved in 5 ml of ethyl acetate whereupon a solution of 0.16 g/0.9 millimole, 2 equivalents/of p-toluenesulfonic acid monohydrate and 2 ml of ethyl acetate is added. The suspension is stirred first at room temperature whereupon the precipitation of crystals is rendered complete at 0-5° C. The product is filtered, washed with some ethyl acetate dried in vacuo to constant weight. Thus 0.15 g (42%) of the title compound are obtained. Mp.:175-178° C.

IR (KBr): 3336, 3167, 1724, 1685, 1657, 1610, 1213, 1182, 1011 cm$^{-1}$.

HNMR (DMSO-d$_6$, 400 MHz): 8.92 (br s, 2H), 8.55 (br s, 2H), 8.36 (m, 1H), 7.77 (d, J=8.6 Hz, 1H), 7.68 (d, J=9.0 Hz, 2H), 7.61 (m, 1H), 7.59 (m, 1H), 7.49 (b, 1H), 7.49 (d, J=8.1 Hz, 2H), 7.39 (dd, J$_1$=1.5 Hz, J$_2$=8.6 Hz, 1H), 7.16 (m, 1H), 7.11 (d, J=7.9 Hz, 2H), 7.06 (m, 1H), 6.88 (d, J=9.0 Hz, 2H), 4.94 (s, 2H), 4.2 (t, J=7.0 Hz, 2H), 3.97 (q, J=7.1 Hz, 2H), 3.92 (s, 3H), 2.70 (t, J=7.0 Hz, 2H), 2.28 (s, 3H), 1.12 (t, J=7.0 Hz, 3H).

Example 11

Preparation of the 1:2 p-toluenesulfonic acid salt of ethyl-N-[(2-{[(4-carbamimidoylphenyl)amino]metil}-1-methyl-1H-benzimidazole-5-yl)-carbonyl]-N-pyridine-2-yl-β-alaninate (2) from the 1:1 oxalate salt of ethyl-N-{[1-methyl-2-({[4-(5-methyl-1,2,4-oxadiazole-3-yl)-phenyl]amino}-methyl)-1H-benzimidazole-5-yl]carbonyl}-N-pyridine-2-yl-β-alaninate (15, R is methyl)

Into a 80 ml pressure tight steel reactor 1.5 g (2.4 millimoles) of the 1:1 oxalic acid salt of ethyl-N-{[1-methyl-2-({[4-(5-methyl-1,2,4-oxadiazole-3-yl)phenyl]amino}methyl)-1H-benzimidazole-5-yl]carbonyl}-N-pyridine-2-yl-β-alaninate (15*(COOH)$_2$, R is methyl), 25 ml of ethanol, 2.5 ml of acetic acid and 0.30 g of a 5% palladium-charcoal catalyst are weighed in. After inertization there reaction mixture is hydrogenated at 50° C. under a pressure of 5 bar for 24 hours. The reaction mixture is filtered and the solvent is removed. The crude product is dissolved in 15 ml of ethyl acetate whereupon a solution of 0.82 g (4.3 millimoles, 1.8 equivalents) of p-toluenesulfonic acid monohydrate and 10 ml of ethyl acetate is added. The suspension is stirred first at room temperature and then crystallized at 0-5° C. The product is filtered, washed with some ethyl acetate and dried in vacuo to constant weight. Thus 1.00 g (50%) of the title compound are obtained. Mp.: 175-176° C.

IR (KBr): 3336, 3167, 1724, 1685, 1657, 1610, 1213, 1182, 1011 cm$^{-1}$.

HNMR (DMSO-d$_6$, 400 MHz): 8.92 (br s, 2H), 8.55 (br s, 2H), 8.36 (m, 1H), 7.77 (d, J=8.6 Hz, 1H), 7.68 (d, J=9.0 Hz, 2H), 7.61 (m, 1H), 7.59 (m, 1H), 7.49 (b, 1H), 7.49 (d, J=8.1 Hz, 2H), 7.39 (dd, J$_1$=1.5 Hz, J$_2$=8.6 Hz, 1H), 7.16 (m, 1H), 7.11 (d, J=7.9 Hz, 2H), 7.06 (m, 1H), 6.88 (d, J=9.0 Hz, 2H), 4.94 (s, 2H), 4.2 (t, J=7.0 Hz, 2H), 3.97 (q, J=7.1 Hz, 2H), 3.92 (s, 3H), 2.70 (t, J=7.0 Hz, 2H), 2.28 (s, 3H), 1.12 (t, J=7.0 Hz, 3H).

Example 12

Preparation of ethyl-3-{[(2-{[(4-{N″[hexyloxycarbonyl]-carbamimidoyl}-phenyl)amino]methyl}-1-methyl-1H-benzimidazole-5-yl)carbonyl]-(2-pyridinyl)amino-propanoate (1) from the 1:2 p-toluenesulfonic acid salt of ethyl-N-[(2-{[(4-carbamimidoylphenyl)amino]methyl}-1-methyl-1H-benzimidazole-5-yl)-carbonyl]-N-pyridine-2-yl-β-alanianate Into a 2000 ml round-bottomed flask equipped with a mechanical stirrer 175 ml of water, 105 ml of acetone and 105 ml of ethanol are weighed in, whereupon 42.6 g (0.308 mole) of potassium carbonate are dissolved in the mixture. 35.0 g (0.041 mole) of the 1:2 p-toluene sulfonic acid salt of 1-methyl-2-[N-(4-amidino-phenyl)-aminomethyl]-5-benzimidazole-carboxylic acid-N-[2-methoxycarbonyl)-ethyl]-amide are added and the mixture is warmed to 28-32° C. A solution of 8.5 ml of chloro hexyl formiate in 30 ml of acetone is added whereupon the reaction mixture is stirred at 28-32° C. for 20 minutes. After the addition of 700 ml of ethyl acetate the two-phase system obtained is separated, the organic layer is washed with water (three times 350 ml each) pre-warmed to 60-65° C. and the solution is concentrated. To the solution a further amount (350 ml) of ethyl acetate is added and the solution is concentrated again. To the solution 630 ml of a 4:1 solvent mixture of cyclohexane and ethyl acetate are added. The mixture is allowed to cool to room temperature and stirred at this temperature for 30-60 minutes. The product is filtered, washed with a 3:2 solvent mixture of cyclohexane and ethyl acetate (twice 90 ml each) and dried. Thus 22.0 g (85%) of the title compound are obtained. The analytical sample of the product is obtained after recrystallization. Mp.: 125-128° C.

IR (KBr): 3408, 3381, 1730, 1611, 1471, 1258, 1143 cm$^{-1}$.

$^1$H-NMR (DMSO-d$_6$, 500 MHz): 8.50-9.30 (bs, 2H), 8.39 (dd, 1H), 7.80 (d, 2H), 7.53 (dt, 1H), 7.47 (d, 1H), 7.40 (d, 1H), 7.12 (m, 2H), 6.95 (t, 1H), 6.68 (d, 1H), 6.75 (d, 2H), 4.60 (d, 2H), 4.22 (t, 2H), 3.97 (m, 4H), 3.77 (s, 3H), 2.68 (t, 2H), 1.58 (m, 2H), 1.29 (m, 6H), 1.12 (t, 3H), 0.86 (t, 3H) ppm.

The invention claimed is:

1. A process for preparing dabigatran etexilate of Formula (1)

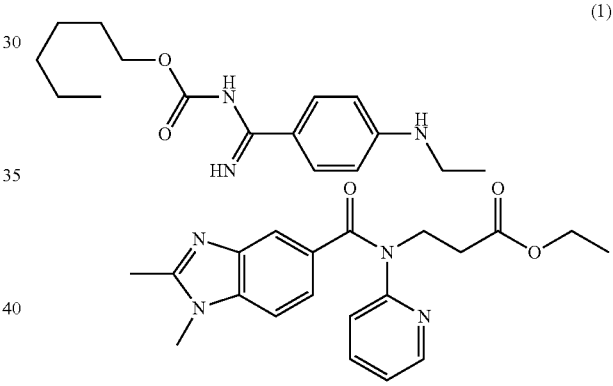

(1)

or a pharmaceutically acceptable salt thereof which comprises reducing a compound of Formula (15)

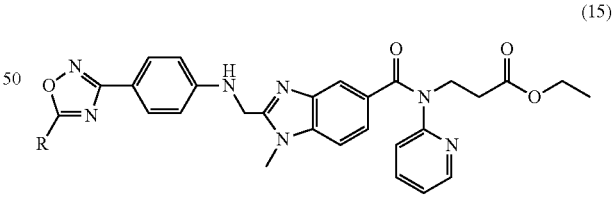

(15)

wherein

R stands for hydrogen;

C$_{1-6}$ straight or branched chain, saturated or partially or completely un-saturated hydrocarbon chain, C$_{1-6}$ straight or branched chain, partially or completely halogenated alkyl;

aryl or methoxymethyl;

optionally converting the thus obtained compound of Formula (2)

into a salt and reacting the compound of Formula (2) or a salt thereof with chloro hexyl formate to yield the compound of Formula (1) and optionally forming a salt from the compound of Formula (1).

2. A process according to claim 1, which comprises carrying out reduction by catalytic hydrogenation, in the presence of an acid.

3. A process according to claim 1, which comprises adding for the formation of a salt of the compound of Formula (2) a further acid.

4. A product, which is a compound of Formula (15)

wherein
R stands for hydrogen;
$C_{1-6}$ straight or branched chain, saturated or partially or completely un-saturated hydrocarbon chain,
$C_{1-6}$ straight or branched chain, partially or completely halogenated alkyl;
aryl or
methoxymethyl
or a salt thereof.

5. A product according to claim 4, which is the monooxalate salt of a compound of Formula (15)

wherein
R is methyl.

6. A process for preparing a compound of Formula (15) according to claim 4 or a salt thereof, which comprises coupling a compound of Formula (14)

or a salt thereof wherein
R stands for hydrogen;
$C_{1-6}$ straight or branched chain, saturated or partially or completely un-saturated hydrocarbon chain,
$C_{1-6}$ straight or branched chain, partially or completely halogenated alkyl;
aryl or
methoxymethyl,
with the compound of Formula (5)

and carrying out ring closure of the benzimidazole ring.

7. A process according to claim 6, which comprises carrying out coupling and ring-closure in a one-step process.

8. A process according to claim 1, which comprises carrying reduction by catalytic hydrogenation with a palladium charcoal catalyst in the presence of an acid.

9. A process according to claim 1, which comprises carrying reduction by catalytic hydrogenation in the presence of acetic acid.

10. A process according to claim 1, which comprises carrying reduction by catalytic hydrogenation with a palladium charcoal catalyst in the presence of acetic acid.

11. A process according to claim 1, which comprises adding for the formation of a salt of the compound of Formula (2) p-toluenesulfonic acid to yield the ditosylate salt of the compound of Formula (2).

12. A process according to claim 1, which comprises adding for the formation of a salt of the compound of Formula (2) p-toluenesulfonic acid in a 2-6 molar equivalent amount to yield the ditosylate salt of the compound of Formula (2).

13. A process according to claim 1, which comprises adding for the formation of a salt of the compound of Formula (2) p-toluenesulfonic acid in a 2-4 molar equivalent amount to yield the ditosylate salt of the compound of Formula (2).

14. A process according to claim 6, which comprises carrying out coupling and ring-closure in a one-step process by an acylation promoter.

15. A process according to claim 6, which comprises carrying out coupling and ring-closure in a one-step process by an acylation promoter selected from the group consisting of 1,1'-carbonyl-diimidazole (CDI) and propyl phosphonic acid anhydride (T3P).

16. A process according to claim 1, which comprises converting the compound of Formula (2) into a salt.

17. A process for preparing dabigatran etexilate of Formula (1)

(1)

[Structure of Formula (1)]

or a pharmaceutically acceptable salt thereof
which comprises coupling a compound of Formula (14)

(14)

[Structure of Formula (14)]

or a salt thereof
wherein
R stands for hydrogen;
  $C_{1-6}$ straight or branched chain, saturated or partially or completely un-saturated hydrocarbon chain,
  $C_{1-6}$ straight or branched chain, partially or completely halogenated alkyl;
  aryl or
  methoxymethyl,
with the compound of Formula (5)

(14)

[Structure of Formula (14)]

and carrying out ring closure of the benzimidazole ring, and reducing the thus obtained compound of Formula (15)

wherein
R stands for hydrogen;
  $C_{1-6}$ straight or branched chain, saturated or partially or completely un-saturated hydrocarbon chain,
  $C_{1-6}$ straight or branched chain, partially or completely halogenated alkyl;
  aryl or
  methoxymethyl;
optionally converting the thus obtained compound of Formula (2)

(2)

[Structure of Formula (2)]

into a salt and reacting the compound of Formula (2) or a salt thereof with chloro hexyl formate to yield the compound of Formula (1) and optionally forming a salt from the compound of Formula (1).

18. A process according to claim 17, which comprises carrying out reduction by catalytic hydrogenation, in the presence of an acid.

19. A process according to claim 17, which comprises adding for the formation of a salt of the compound of Formula (2) a further acid.

20. A process according to claim 1, wherein the compound of formula 15 is the monooxalate salt of said compound of Formula (15)

(15)

[Structure of Formula (15)]

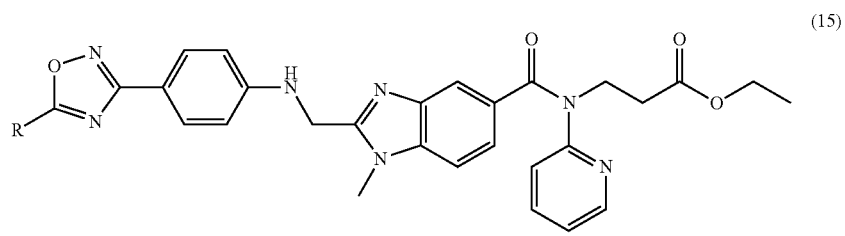

(15)

wherein
R is methyl.

21. A process according to claim 1, wherein in the compound of formula 15, R stands for hydrogen.

22. A process according to claim 1, wherein in the compound of formula 15, R stands for $C_{1-6}$ straight or branched chain, saturated or partially or completely un-saturated hydrocarbon chain.

23. A process according to claim 1, wherein in the compound of formula 15, R stands for $C_{1-6}$ straight or branched chain, partially or completely halogenated alkyl.

24. A process according to claim 1, wherein in the compound of formula 15, R stands for aryl.

25. A process according to claim 1, wherein in the compound of formula 15, R stands for methoxymethyl.

26. A process according to claim 1, which is for the industrial scale manufacturing of dabigatran etexilate of Formula (1) or a pharmaceutically acceptable salt thereof.

* * * * *